US006287608B1

(12) United States Patent
Levin et al.

(10) Patent No.: US 6,287,608 B1
(45) Date of Patent: Sep. 11, 2001

(54) METHOD AND APPARATUS FOR TREATMENT OF CONGESTIVE HEART FAILURE BY IMPROVING PERFUSION OF THE KIDNEY BY INFUSION OF A VASODILATOR

(75) Inventors: Howard R. Levin, Teaneck, NJ (US); Mark Gelfand, New York, NY (US)

(73) Assignee: Intellicardia, Inc., New York, NY (US)

( * ) Notice: Subject to any disclaimer, the term of this patent is extended or adjusted under 35 U.S.C. 154(b) by 0 days.

(21) Appl. No.: 09/547,104

(22) Filed: Apr. 11, 2000

(51) Int. Cl.$^7$ .................................................. A61K 33/00
(52) U.S. Cl. ............................................................ 424/718
(58) Field of Search ............................................. 424/718

(56) References Cited

U.S. PATENT DOCUMENTS

| | | | |
|---|---|---|---|
| 4,710,164 | 12/1987 | Levin et al. | 604/66 |
| 4,762,820 | 8/1988 | Gavras | 514/10 |
| 5,045,057 | 9/1991 | Van Driessche et al. | 604/50 |
| 5,167,628 | 12/1992 | Boyles | 604/101 |
| 5,290,227 | 3/1994 | Pasque | 600/16 |
| 5,308,319 | 5/1994 | Ide et al. | 600/18 |
| 5,326,374 | 7/1994 | Ilbawi et al. | 623/3 |
| 5,332,403 | 7/1994 | Kolff | 600/16 |
| 5,505,701 | 4/1996 | Anaya Fernandez de Lomana | 604/99 |
| 5,536,237 | 7/1996 | Prince et al. | 604/4 |
| 5,755,779 | 5/1998 | Horiguchi | 623/1 |
| 5,776,190 | 7/1998 | Jarvik | 623/3 |
| 5,869,539 | 2/1999 | Garfield et al. | 514/746 |
| 5,902,336 | 5/1999 | Mishkin | 623/11 |
| 5,957,880 | 9/1999 | Igo et al. | 604/4 |
| 6,086,527 | 7/2000 | Talpade | 600/18 |

FOREIGN PATENT DOCUMENTS 199 01 078   1/1999  (DE) .

OTHER PUBLICATIONS

Elkayam et al. "Renal vasodilatory effect of endothelial stimulation in patient s with chronic congestive heart failure" Journal of the American College of Cardiology, Jul. 1996, vol. 28(1) 176–82. ISSN:0735–1097.*

Pawlik et al. "Effects of Dimaprit prostacyclin and acetyl choline on renal blood flow and function"; Proc Soc Exp Biol Med, 1980 163(3), p. 344–349. CODEN: PSEBAA. ISSN: 0037–9727.*

Pawlik et al, Effects of Dimaprit, Prostacyclin, and Acetylcholine on Renal Blood Flow and Function, *Proceedings of the Society for Experimental Biology and Medicine*, 163, 344–349 (1980), pp. 344–349.

* cited by examiner

*Primary Examiner*—Theodore J. Criares
*Assistant Examiner*—Jennifer Kim
(74) *Attorney, Agent, or Firm*—Nixon & Vanderhye P.C.

(57) ABSTRACT

A method for treating congestive heart failure (CHF) has been developed that restores kidney renal functions by artificial vasodilation of at least one kidney. A vasodilator drug is locally delivered to the kidney via a kidney perfusion catheter. The drug can be mixed with the patient's blood, saline or other suitable solvent and the mixture directly applied to the kidney through the catheter. The restoration of kidney function assists the heart by removing excess fluid, urine and toxin from the patient, and by normalizing the patient's renin-angiotensin system and other neurohormonal substances. The method is applicable to treat chronic and acute CHF.

26 Claims, 7 Drawing Sheets

METHOD AND APPARATUS FOR TREATMENT OF CONGESTIVE HEART FAILURE BY IMPROVING PERFUSION OF THE KIDNEY BY INFUSION OF A VASODILATOR

FIELD OF THE INVENTION

The invention generally relates to the treatment of kidneys by direct application of a vasodilator agent. In particular, the invention relates to a method and apparatus to treat patients with congestive heart failure by reducing resistance to blood flow to the patient's kidney by direct infusion of a vasodilator drug.

BACKGROUND OF THE INVENTION

A. Congestive Heart Failure

Congestive heart failure (CHF) is a serious condition affecting an estimated 5 million Americans. Increasing prevalence, hospitalizations, and deaths have made CHF a major chronic health condition in the United States. There are an estimated 400,000 new cases of CHF each year. These cases are often first diagnosed as the end stage of cardiac disease. The average mortality rate of CHF is 10 percent after the 1st year and 50 percent after 5 years. Thus, half of the patients diagnosed with CHF will die within 5 years of their diagnosis.

The magnitude of the problem is expected to get much worse as more cardiac patients are able to survive and live longer. As patients live longer, the potential for developing CHF increases. In addition, because the incidence of heart failure rises substantially beyond age 65, the prevalence of this condition is likely to increase as the population ages.

The high prevalence of heart failure and the resulting high cost of caring for these patients places a significant economic burden on society. The American Heart Association statistics report that, including medications, an estimated $22.5 billion will be spent for the care of CHF patients in hospitals, physicians offices, home care, and nursing homes including medications in the year 2000. In light of the high costs and poor prognosis of CHF, there is a pressing need to prevent this condition and provide better clinical management to reduce morbidity and mortality.

Congestive heart failure (CHF) is a diseased condition in which the heart fails to function efficiently as a pump to provide sufficient blood flow and/or pressure to fulfill the normal circulatory needs of a patient. CHF results in sudden shortness of breath, fainting and irregular heart beats that require frequent emergency room treatments (acute CHF), and in its chronic form leads to repeated hospital stays, deteriorating quality of life and significant costs to the health care system. Congestive heart failure is characterized by: (1) signs and symptoms of intravascular and interstitial volume overload, including shortness of breath, fluid in the lungs, and edema, and (2) manifestations of inadequate tissue perfusion, such as fatigue or poor exercise tolerance. These signs and symptoms result when the heart is unable to generate a cardiac output sufficient to meet the body's demands.

In CHF, the failing heart is not able to generate sufficient blood pressure to properly perfuse the kidneys, e.g., provide sufficient blood pressure to force blood through the kidneys and filter the blood. In a patient suffering from chronic heart failure, the blood pressure tends to progressively decrease as the heart progressively fails over weeks, months or years. With the decrease in blood pressure there is a concomitant decrease in organ perfusion. Accordingly, chronic heart failure can lead to chronic impaired renal perfusion.

Chronic heart failure patients frequently evolve into acute CHF and are admitted to hospital with an abrupt worsening of their condition. During these periods of acute hypotension (or low blood pressure) their kidneys are particularly at risk from decreased renal blood flow and may be severely injured. In some cases the blood pressure of these patients can be normal but at the expense of the total shutdown of the blood flow to the kidneys.

B. Relationship of Kidney Failure to CHF

The kidneys are a pair of organs that lie in the back of the abdomen on each side of the vertebral column. They play an important regulatory role in maintaining the homeostatic balance of the body. The kidneys function like a complex chemical filtering plant. They eliminate foreign chemicals from the body, regulate inorganic substances and the extracellular fluid, and function as endocrine glands, secreting hormonal substances like renin and erythropoietin.

The main functions of the kidney are to maintain the water balance of the body and control metabolic homeostasis. The kidneys regulate the amount of fluid in the body by making the urine more or less concentrated, thus either reabsorbing or excreting more fluid, respectively. The kidneys also extract undesirable chemicals and concentrate them in urine, while allowing the reabsorption of other chemicals.

The kidney processes of filtration, reabsorption and fluid regulation take place in the renal nephron of the kidney. Within the nephron the smallest circulatory vessels, capillaries and arterioles, form a glomerulus. The glomerulous is intimately associated with the renal tubules to filter wastes from the blood, remove excess water from the body and produce concentrated urine. The glomerular filtration rate (GFR) is a clinical indicator universally accepted as a measure of the ability of the kidney to remove fluid and solutes. GFR is the summary of the physiologic functions of the kidneys.

The kidneys remove the deleterious metabolic products from the blood, which represents a small portion of the total blood volume. The blood is repeatedly circulated through the kidney several times during each day to remove the required amount of these deleterious metabolic products. In a healthy person, the kidney receives approximately 10% of the cardiac output which is the total body blood flow (about 0.5 liters per minute) which, over the course of a day, amounts to 720 liters per day of blood passing through each kidney. Significantly more blood fluid is filtered through the kidneys than is excreted as urine. Most of the filtered blood fluid must be reabsorbed into the circulatory system to maintain the fluid balance of the body.

Without properly functioning kidneys, a patient will suffer water retention, reduced urine flow and an accumulation of wastes toxins in the blood and body. These conditions resulting from reduced renal function or renal failure (kidney failure) are believed to increase the workload of the heart. In a CHF patient, renal failure because of decreased renal perfusion will cause the heart to further deteriorate. Water and blood toxins accumulate due to the poorly functioning kidneys and in turn, cause the heart further harm.

Fluid overload during CHF is caused in two ways. First, activation of neurohormonal mechanisms of the renin-angiotensin system and aldosterone activation leads to peripheral vasoconstriction and retention of salt, thus water by the kidney. Second, the persistent lower renal blood flow and pressure cannot generate adequate hydrostatic pressure to make sufficient urine to remove excess retained fluid.

Accordingly, the kidneys are a principal non-cardiac cause of a progressive fluid overload condition in a patient suffering from CHF.

Patients with CHF can also suffer episodes of acute, severe deterioration caused by abrupt decreases in heart function. These episodes are characterized by rapid reductions in blood pressure and flow, especially to the kidney. Similarly to the chronic state, acutely reduced kidney perfusion can result in a sudden, massive retention of fluid leading to pulmonary edema (fluid in lungs). This acute fluid overload taxes an already overburdened heart and can lead to the severest of complications: acute renal failure and death.

C. Prior Kidney Treatments for CHF

To treat CHF, the physicians must fight the body's attempt to inflict itself harm. Physicians can treat the patient with medications that improve the pumping ability of the heart, increase blood pressure and attempt to reactivate a more normal behavior of the body's control (homeostatic) system. Heart failure patients are put on a strict low sodium diet and their fluid intake is monitored. Some patients are limited to as little as one liter of fluid a day. Diuretics are a class of drugs that combat fluid overload. Diuretics affect the kidney function in such a way that the reabsorption of fluid is suppressed. As a result there is more urine output contrary to neurohormonal commands that the kidney is receiving.

When diet, diuretics, and other treatments can no longer achieve adequate fluid removal with existing kidney function, renal replacement therapies such as hemofiltration or dialysis have been increasingly used as a method of removing fluid in the acute CHF state. Acute heart failure can be treated with the Continuous Renal Replacement Therapy (a.k.a. an artificial kidney or dialysis machine) in the ICU (intensive care unit) of a hospital. A dialysis machine is instrumental in reducing fluid overload and preventing such complications as pulmonary edema. However, the dialysis machine can be harmful to other organs and does not protect the kidney itself from further deterioration from the persistently low blood pressure and poor perfusion caused by vasoconstriction of the renal artery and arterioles (smaller branches). Further, renal replacement therapy may be used to remove fluid but is associated with significant complications. Renal replacement is limited since it may cause further abrupt reductions in blood pressure, actually worsening the heart failure state and further renal dysfunction. Physicians are also reluctant to use replacement therapy in unstable patients because of added risk of hypotension.

Continuous hemofiltration is based on the well-established therapy with an artificial kidney (or renal replacement therapy). Blood is continuously extracted from the body, passed through an artificial kidney machine and then returned back to the body. In this hemofiltration process, some of the undesired chemicals can be extracted from the blood. Most importantly for acute heart failure patients, fluid can be filtered out of the blood stream in a slow controlled infusion while concentrating the blood.

Reversing fluid overload can improve heart function and significantly enhance the clinical status of the CHF patient. While therapies, such as hemofiltration, remove fluid from the patient, they can actually lead to lower blood pressure, further deterioration of the heart and ultimately renal failure requiring the patient to undergo permanent dialysis or kidney transplant.

D. Vasodilators in Heart Failure

Until recent years, the therapy of heart failure was devoted to restoring contractility with cardiac glycosides and relieving congestion and edema with diuretics. The additional use of vasodilating agents has been shown to be valuable where conventional therapy alone has been ineffective. The role of vasodilators as first line agents is now more firmly established.

In a CHF, the reduction in cardiac output causes the peripheral resistance to rise in the vascular system in order to maintain perfusion pressure to vital organs. This compensatory increase in peripheral resistance is mediated by increased sympathetic tone and angiotensin. This compensatory response sets up a vicious circle whereby a lowered cardiac output leads to vasoconstriction, which, in turn, further reduces cardiac output as the heart fails to cope against the increased peripheral resistance. Arterial vasodilators administered to CHF patients lower aortic impedance (afterload) and, thus, reduce the workload of the heart. This results in a reduced ventricular end-diastolic volume, pressure and wall tension. If the blood vessels are dilated the amount of work needed for the heart to pump blood forward is decreased and heart efficiency enhanced. Administering systemic vasodilators either orally or added directly to the bloodstream via a bolus IV injection or drip is beneficial to the CHF patient and particularly important to the kidney function. Vasodilatation of renal blood vessels results in increased renal plasma flow, improved renal function, and reduction of the secretion of renin.

Unfortunately in severe heart failure the conventional treatments using vasodilators is limited. The weakened heart has a reduced ability to pump blood and cannot maintain adequate blood pressure. Since the heart can no longer augment its force of contraction, any increase in vasodilation, while beneficial in reducing the work and preserving the heart, has an adverse effect on vital organ perfusion and survival if prolonged. For example, a disadvantage of the conventional treatment of systemic administration, oral or intravenous, is that vasodilators remain in the bloodstream for a prolonged amount of time (until the vasodilators are metabolized or excreted). In view of the problems associated with prolonged retention only very limited amounts of vasodilators can be given to the patient without a risk of severe complications. Even at low or normal doses, commonly clinically used vasodilating agents (such oral compounds as captopril, enalapril or other known class of dilator such as nitroglycerin or the intravenously administered compound sodium nitroprusside) effect the peripheral circulation of blood to the patient's arms, legs, and other peripheral areas. These vasodilating agents reduce systemic vascular resistance and, with a weakened heart incapable of adequately responding to demand, can cause severe hypotension and circulatory collapse.

SUMMARY OF INVENTION

Because of the limited success of the above kidney treatments, there is a long-felt need to be able to treat the fluid overload complications of CHF by restoring natural kidney functions, and without resorting to mechanical kidney dialysis. Restoration of natural kidney functions would advantageously: (1) return kidney function to normal therefore protecting kidney from hypotension induced damage, (2) remove excess fluid volume from a patient in a safe controlled manner, and/or (3) alter a patient's neurohormonal environment. Restoring natural kidney functions in a CHF patient should decrease or eliminate some of the physical signs and symptoms of congestive heart failure, and improve a patient's quality of life and survival rate. There is a need to have a vasodilator therapy where the chemical agent will be delivered directly and only to the kidney and will be removed from circulation or loose its potency upon leaving the kidney or shortly thereafter so that the rest of the peripheral circulation will not be effected.

One of the challenges to developing a new kidney therapy is the large amount of blood that passes through the kidney and quickly circulates through the rest of the body. With the kidney receiving as much as 10% of the total cardiac output a locally administered drug will within minutes be returned to the heart and distributed throughout the circulatory system. Therefore, slowly metabolized vasodilators will continue circulating until the net adverse effect from the local delivery is the same as if the drug was infused systemically.

Also, the systemic blood pressure and flow to a patient's kidney may be insufficient, even in the setting of vasodilator therapy, to allow clinical benefit from the vasodilator therapy. In other patients, the blood flow to the kidney may not be interrupted for prolonged periods of time without causing severe injury. Thus, some patients may also require continuous perfusion of the kidney during infusion of vasodilator therapy to maintain viability of the kidney.

The invention is a kidney treatment which reduces the kidney's resistance to blood flow. The treatment allows for greater perfusion of blood through the kidney. The invention applies a vasodilation agent directly to a kidney using a kidney perfusion catheter. The perfusion catheter is inserted at the entrance to the renal artery and provides a flow of blood at an elevated pressure to perfuse the kidney. A vasodilation agent is added to the perfusion blood flow and, thus, flows directly to the perfused kidney. The vasodilation agent relaxes the kidney so that the vessels through the kidney dilate. The dilated vessels reduce the resistance of the kidney to the perfusing blood flow and allow a greater volume of blood to flow through the kidney.

The invention includes a novel method and apparatus of treating acute and chronic CHF by reduction of the vascular resistance of the blood vessels inside the kidney by infusing a vasodilating agent. Vasodilation is achieved by administration of a vasoactive substance such as nitric-oxide (NO) continuously over a period of time that will yield the desired clinical effect (removal of excessive fluid and normalization of kidney function).

The vasodilator while dissolved in blood, saline or other substance capable of binding the molecules of the vasodilating agent is delivered to the kidney directly via a catheter. The vasodilator breaks down quickly when in contact with blood so that the systemic vasodilation will not follow the vasodilation of the kidney.

SUMMARY OF THE DRAWINGS

A preferred embodiment and best mode of the invention is illustrated in the attached drawings that are described as follows.

DETAILED DESCRIPTION OF A PREFERRED EMBODIMENT OF THE INVENTION

Figure 1:
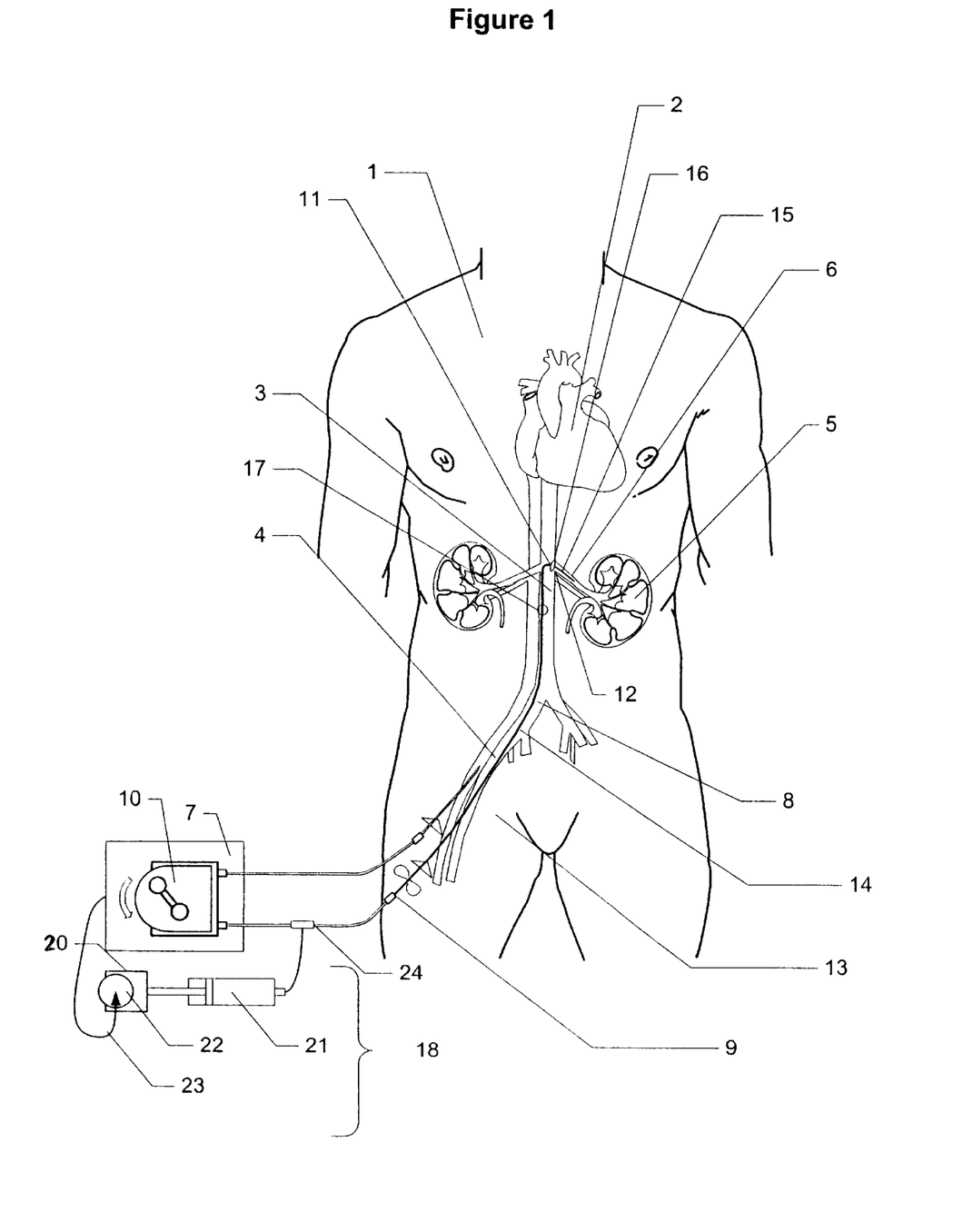
FIG. 1 is a graphical illustration of a patient being treated for CHF by perfusing a kidney with a perfusion catheter and blood pump with a coupled local drug delivery system.

FIG. 1 shows one embodiment of the proposed therapy where the vasodilator drug is used in combination with the apparatus for perfusion of the kidney with a percutaneous catheter. A method and apparatus for isolated perfusion of a kidney with a catheter is described more fully in the co-owned and related U.S. patent application Ser. No. 09/454,605, filed Dec. 7, 1999, for a "Kidney Perfusion Catheter"; and U.S. patent application Ser. No. 09/501,234, filed Feb. 10, 2000, for a "Method and Apparatus for Treatment of Congestive Heart Failure by Improving Perfusion of the Kidney", both of which applications are still pending. The disclosures of both of these patents are incorporated by reference.

FIG. 1 is a schematic diagram of a patient 1 having a heart 2, an aorta 3 a femoral artery 4, a kidney 5, and a renal artery 6. A perfusion catheter assembly 8 is inserted at the patient's groin 13 and into the femoral artery. The catheter, e.g., introducer catheter 14, is maneuvered by a surgeon through the femoral artery, into the aorta to the entrance (ostium 12) of one of the renal arteries 6. The distal end of catheter may include a sealing balloon 16 to block off the entrance of the renal artery and position the catheter at the ostium. Similarly, a positioning balloon 17 may position the catheter within the arota.

Blood enters a proximal end 9 of the catheter from a blood pump 10 and flows from the distal end 11 of the catheter (which may include small diameter catheter tip 15 that extends past the ostium and into the renal artery) directly into the renal artery. Upon exiting the pump, blood is mixed with the fluid containing the vasodilator drug. A drug coupling device 24 connects the drug dispersing apparatus 18 to the proximal end 9 of the catheter, such that the drug can be infused into the blood flowing from the pump 10 to the catheter.

A known dose of the drug is preloaded into an automatic syringe pump 20 and infusion syringe 21. A controller apparatus with a motor 22 is programmed to dispense the drug at a constant rate prescribed by a physician. An optional feature is blood flow rate feedback monitor 23. The rate of the discharge of the drug infusion pump 20, as controlled by the controller 22, can be continuously adjusted based on the rate of the perfusion pump 10. The concentration of the drug in the blood infused into the kidney can be maintained in an amount sufficient to cause vasodilation and be therapeutically effective.

A vasodilator drug is selected for the effective and safe utilization of the treatment would have to have an exceptionally short life after it enters the kidney. Nitric-oxide (NO) is a vasodilator that fits this requirement. After being dissolved in blood, NO is rapidly scavenged by blood cells and remains active only for 8 to 10 seconds. Nitric-oxide (previously called an endothelial derived relaxing factor) is a physiologic regulator of renal hemodynamics. Nitric-oxide is a highly diffusible, reactive free radical. In the body, it is produced in the vascular endothelium and diffuses to the adjacent vascular smooth muscle where it causes vasodilation. Nitric-oxide is continually produced at a basal level in many locations throughout the kidney. Because of the short half-life of nitric-oxide, the location of nitricoxide generation is a major determinant of its site of action. Within the renal circulation, nitric-oxide generated by basal endothelial synthesis vasodilates afferent (pre-glomerular) resistance, efferent (post-glomerular) resistance and the mesangial (important for the rate of filtration) cells. Nitric-oxide therefore increases plasma flow, affects glomerular capillary pressure (PGC) and increases coefficient of ultrafiltration (Kf) by mesangial cell relaxation leading to increase in glomerular filtration rate.

Nitric-oxide is naturally generated by the kidneys to dilate blood vessels and reduce vascular resistance to blood flow. Nitric-oxide is released continuously from endothelial cells in the basal state. The rate of nitric-oxide release increases with increasing blood flow. As the blood flow increases, the shear stress increases due to the blood flowing across the inner surface of the arterial wall. The shear stress on the endothelial cells of the vessel walls stimulates those cells to generate nitric-oxide. As a result, increased amounts of nitric-oxide, among other vasoactive substances, are released. These vasoactive substances cause the arterial smooth muscle vasculature to relax resulting in a flow induced arterial vasodilation. In addition to actively vasodilating the contractile cells of the kidney, nitric-oxide also opposes active vasoconstrictor influences which would otherwise increase the resistance of the kidney to perfusion. Chronic inhibition of nitric-oxide production produces sustained hypertension and renal vasoconstriction, with the eventual development of kidney damage.

NO is widely available in the practice of medicine as gas stored in cylinders under pressure. It has been successfully used in respiratory medicine by mixing the small amounts into the oxygen containing gas mixture administered to the patient by a ventilator. U.S. Pat. No. 5,957,880 discloses an extracorporeal flow circuit (such as a cardiopulmonary bypass machine) where one or more nitric-oxide feeds to provide a concentration of nitric-oxide in the blood effective to inhibit activation of blood platelets and reduce whole body inflammation of the patient induced as a result of a procedure using the extracorporeal circulation. A membrane filter permeable to NO but not to the blood is used to mix NO into the blood. These techniques for infusing NO into a fluid flow from the pump to the catheter are well developed. Such techniques are used in extracorporeal membrane oxygenators to transport oxygen into the blood. These techniques may be used to introduce NO into the blood flow as it is circulated through a blood pump.

Figure 2:
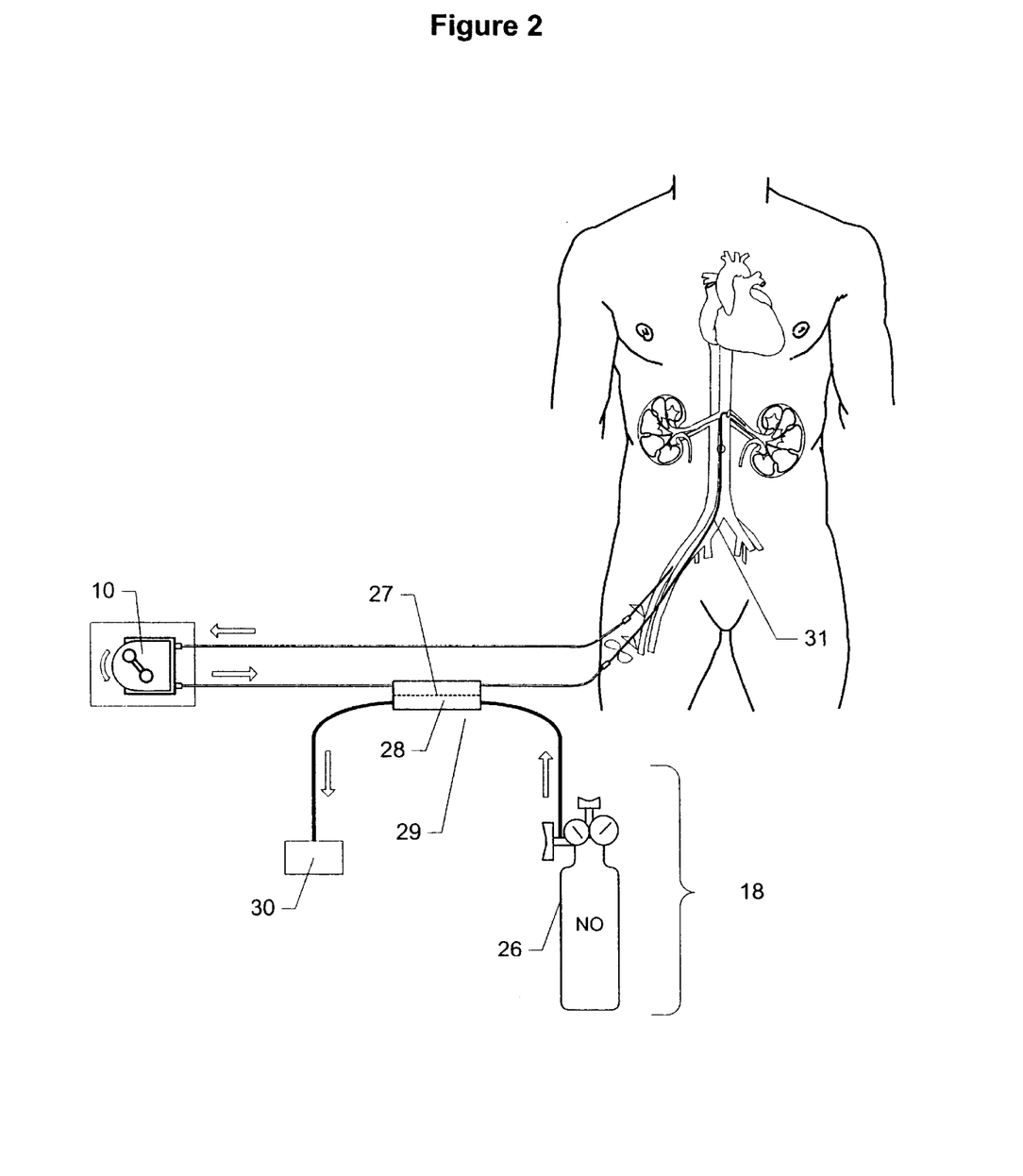
FIG. 2 is a diagram illustrating a catheter perfusion system with a NO gas exchanger.

FIG. 2 shows a kidney catheter assembly 31 with an attachment to introduce nitric-oxide (NO) or other vastrodilator agent into the perfusion fluid flow to a kidney. The cylinder with NO gas 26 provides a positive pressure that infuses NO into the solution through a membrane 27. The infusion of the vastrodilator may be used in conjunction with a blood infusion. NO is forced into a gas compartment 28 of the gas exchange chamber 29. A gas permeable membrane 27 allows molecules of NO to migrate into the blood stream but is not permeable to blood components. Such permeable membranes are well known in the oxygenation of blood and used in heart lung machines and extracorporeal blood oxygenators (ECMO). If NO transfer is from gas to blood a hydrophobic membrane with pores large enough to allow molecules of gas to pass but small enough to stop the water, proteins and other components of blood from passing. If the NO is dissolved in fluid and the molecules are transferred across the membrane using osmotic pressure gradient, the hydrophilic membrane will be used. Suitable hydrophilic membranes are well known and used in dialysis filter for artificial kidney to exchange molecules of chemicals between the blood and the dialysate solution. Such membranes often are manufactured as micro pore fiber bundles and are available for example from Minntech (Minneapolis, Minn.).

To dilute NO it can be mixed with a carrier gas such as Nitrogen or Helium. The pump 10 is the means for regulating the blood flow and prefusion pressure applied to the kidney, and for and indirectly regulating the rate of flow for delivering the nitric oxide gas in an amount sufficient for causing renal vasodilation. In addition a pressure regulator on the cylinder can be used to adjust the flow of gas.

NO is dissolved in a transport solution, e.g., a kidney perfusion fluid, that is biocompatible with blood. Blood is one example of a solvent-transport fluid, but other possible solvent-transport fluids for the delivery of NO to the kidney include, isotonic saline and Krebs solution. The Krebs-Ringer solution is a modification of Ringer's solution, prepared by mixing NaCl, KCl, CaCl2, $MgSO_4$, and phosphate buffer. Since NO is toxic in high concentrations, the unused quantity of gas can be collected into a vacuum chamber 30. NO is harmless if released later into atmosphere. A simple pressure regulator can be used to control flow of NO gas into the filter 27 while the speed of the pump 10 can be used to maintain the desired kidney perfusion pressure. In this way both the kidney vascular resistance and perfusion pressure can be manipulated to achieve the desired renal blood flow that is the determining factor of the kidney function (GFR).

Figure 3:
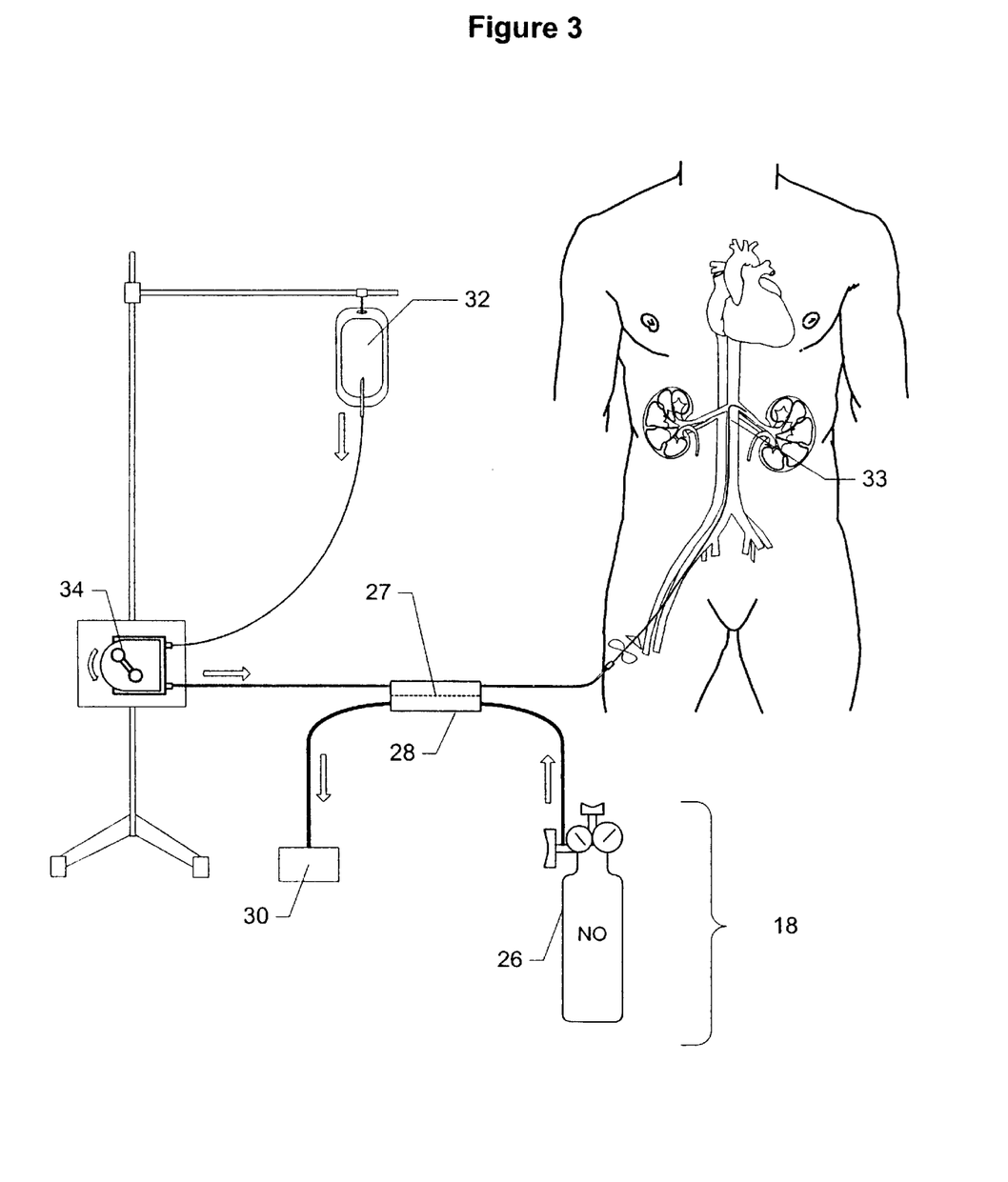
FIG. 3 is a diagram illustrating a drug delivery system without a perfusion pressure delivery system.

FIG. 3 shows another embodiment of a drug dispensing apparatus 18 where NO or other vasodilator drug is dissolved in a solution. For NO, a solute can be as simple as sterile saline or a more complex and specialized compound such as a fluorocarbon emulsion. One representative of blood-type fluorocarbon emulsions is Fluosol manufactured in Japan by Green Cross Corporation and consisting of Perfluorodecalin, Perflurotripropylamine (oxygen carriers), surfactants, and osmotic balance ions. Fluosol has capacity to bind the nitric oxide that is several times higher than that of water or saline. Newer Perfluro Carbon emulsions that can bind NO and Oxygen and are more bio-compatible than Fluosol were disclosed in detail in the U.S. Pat. No. 5,869, 539. The solution is in the container 32 and flows through the pump into the catheter 33. The catheter 33 is non-occluding drug delivery catheter and can be as small as 1 mm in diameter. The infusion pump 34 slowly infuses the solution into the renal artery. Substantial blood flow going from aorta into the kidney will pick up the substance and carry it downstream into the kidney.

Figure 7:
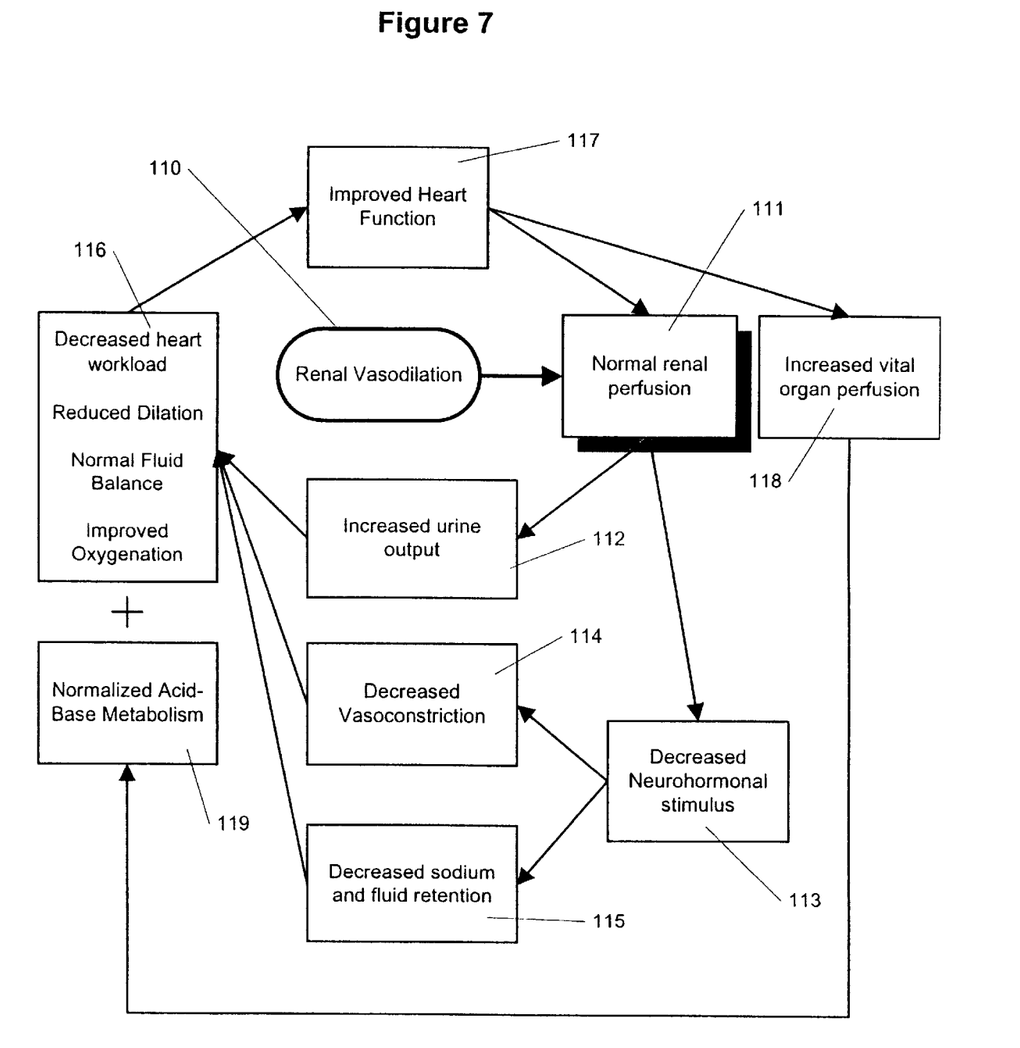
FIG. 7 is a flow diagram and illustration of the remedial effects of direct vasodilator therapy on the cycle of CHF.

Restoration of acceptable renal resistance by the local delivery of vasodilator applied directly applied to one or both kidneys of a patient with heart failure significantly improves renal blood flow, removes excess body fluids and improve the patient's overall condition. In addition, restoring renal blood flow to the kidney suppresses the deleterious activation of the renin-angiotensin system and the consequences of its widespread adverse effects on CHF patients as is shown in FIG. 7.

Figure 4:
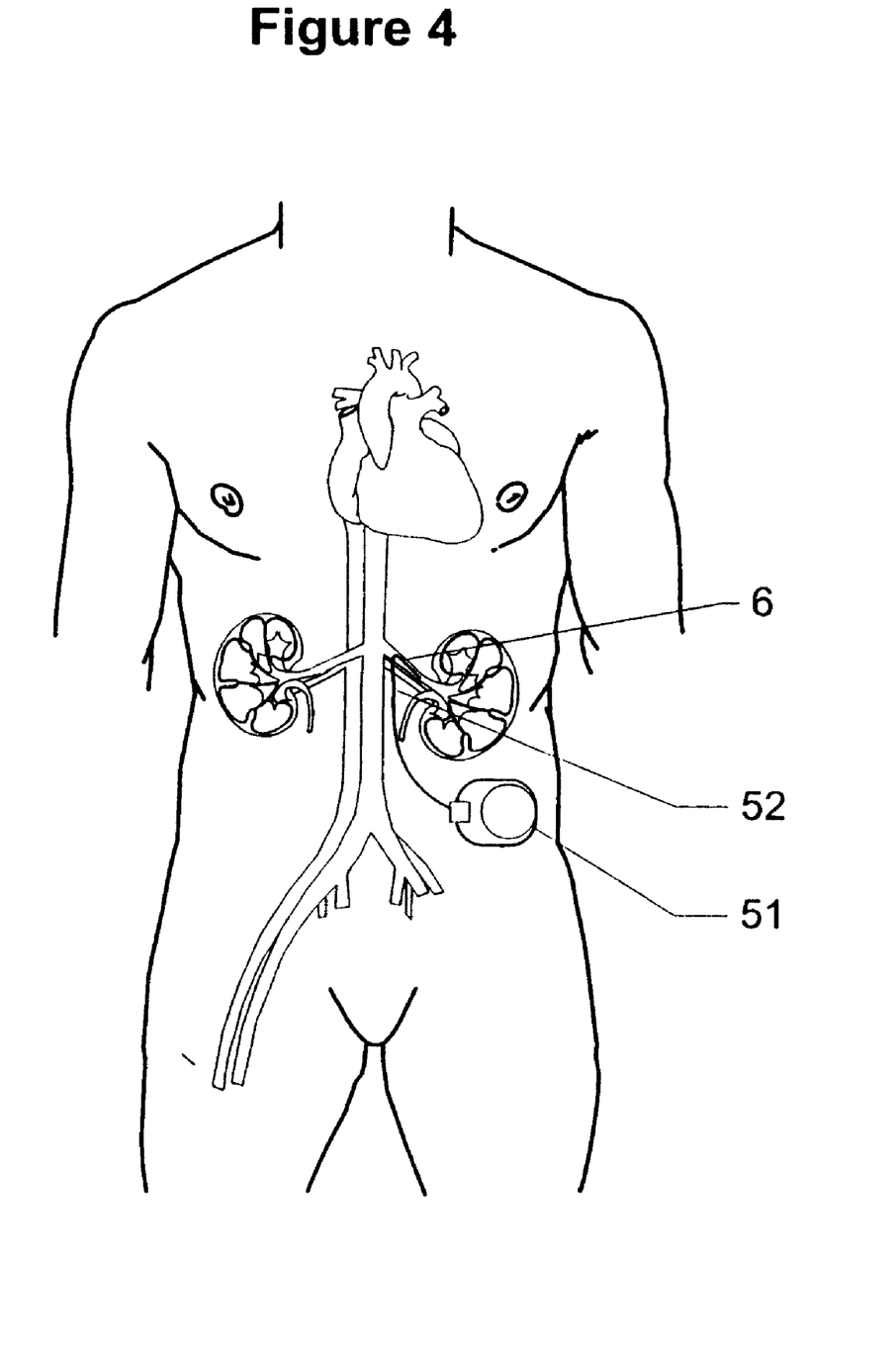
FIG. 4 is an implantable pump for delivery of vasodilator connected to a renal artery.

FIG. 4 shows an implanted embodiment of the present invention. A battery operated microprocessor controlled pump 51, similar to known insulin injection pumps, is subcutaneously implanted in the body. An internal kidney catheter 52 is grafted to the renal artery 6. NO or other vasodilator drug is dissolved in the fluid contained in the reservoir inside the pump. Periodically the reservoir can be refilled by puncturing the patient's skin with a syringe. A special port on the pump receives the injection and seals after the needle is withdrawn.

Figure 5:
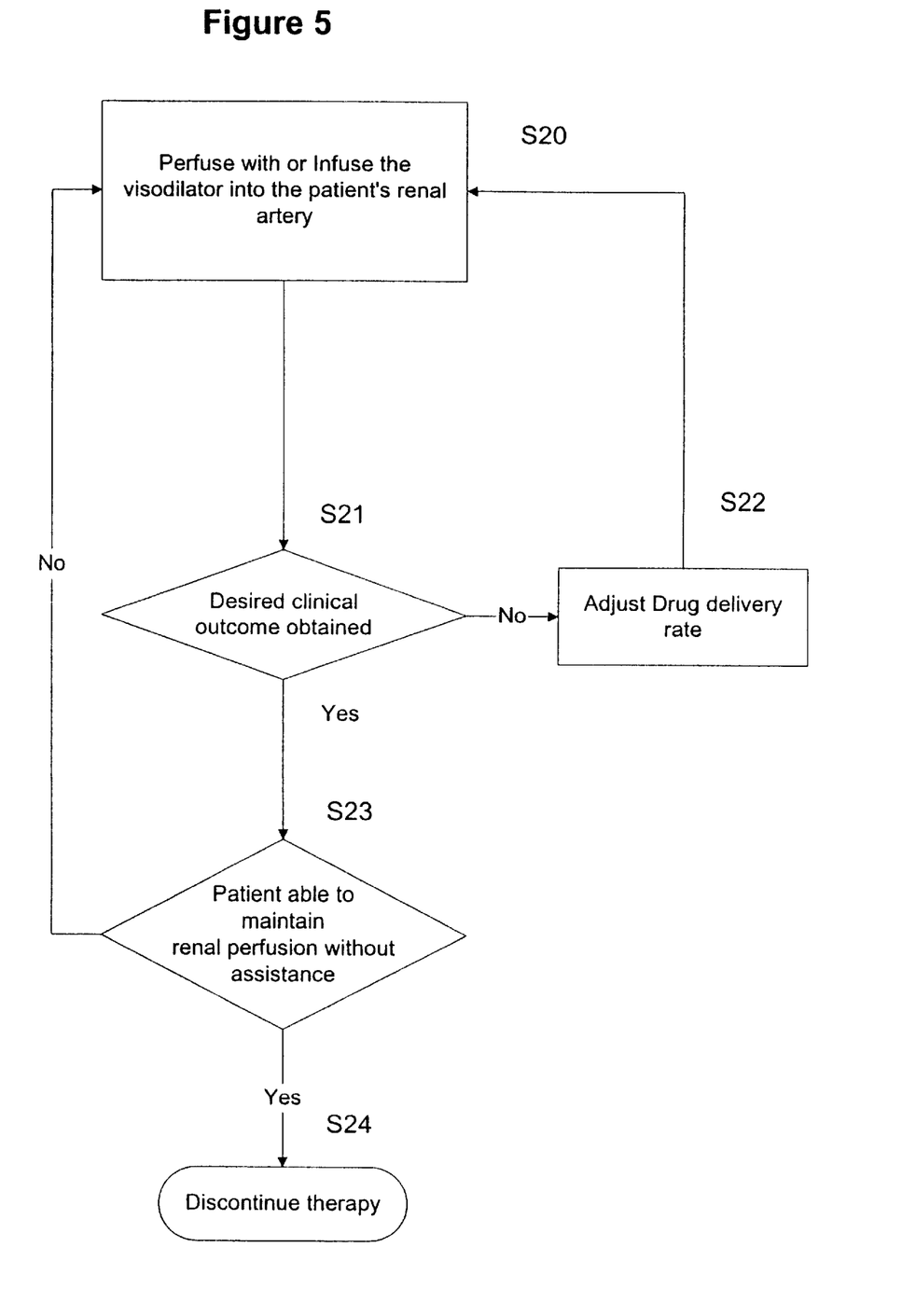
FIG. 5 is a flow chart for a method of vasodilating a patient's kidney with local drug delivery to achieve a desired condition of the patient.

FIG. 5 is a flow chart for a method of infusing the vasodilator into the patient's kidney to achieve a desired condition of the patient. The vasodilator drug is infused into the patient's renal artery such as using a kidney perfusion catheter apparatus shown in different embodiments in FIGS. 1 through 4, in step 20. During the treatment of the vasodilator, the patient is continually monitored, in step 21, to determine whether the desired clinical outcome has been obtained. For example, the desired clinical outcome may be increased urine output from the patient. There may be other desired clinical outcomes, such as sufficient decrease in water retention, changes in blood pressure, or other conditions of the patient which can be clinically monitored by the doctor and that reflect effective treatment by the vasodilator drug.

If the desired clinical outcome is not obtained in a reasonable amount of time, as determined by the doctor, then in step 22 the drug infusion rate is adjusted and the vasodilator treatment is continued. Monitoring of the patient continues and the doctor or other healthcare professional continues to determine whether the desired clinical outcome has been attained. Accordingly, a cycle is set up in which the vasodilator infusion rate is adjusted, possibly on several occasions, until the desired clinical outcome is attained in the patient. When the desired clinical outcome is attained in the patient, the vasodilator treatment and kidney perfusion treatment is terminated in step 23. The patient is further monitored to confirm that the patient is able to maintain sufficient renal perfusion naturally without the assistance of the kidney perfusion catheter. If natural renal perfusion does not occur, then the kidney perfusion therapy and the infusion of the vasodilator drug is resumed in step 20. Preferably, the patent is able to maintain renal perfusion naturally, in step 24, so that both the kidney perfusion therapy and the infusion of vasodilator drugs can be discontinued. Although not shown in FIG. 5, the doctor may at any time discontinue the vasodilator treatment if such treatment is deemed ineffective.

Figure 6:
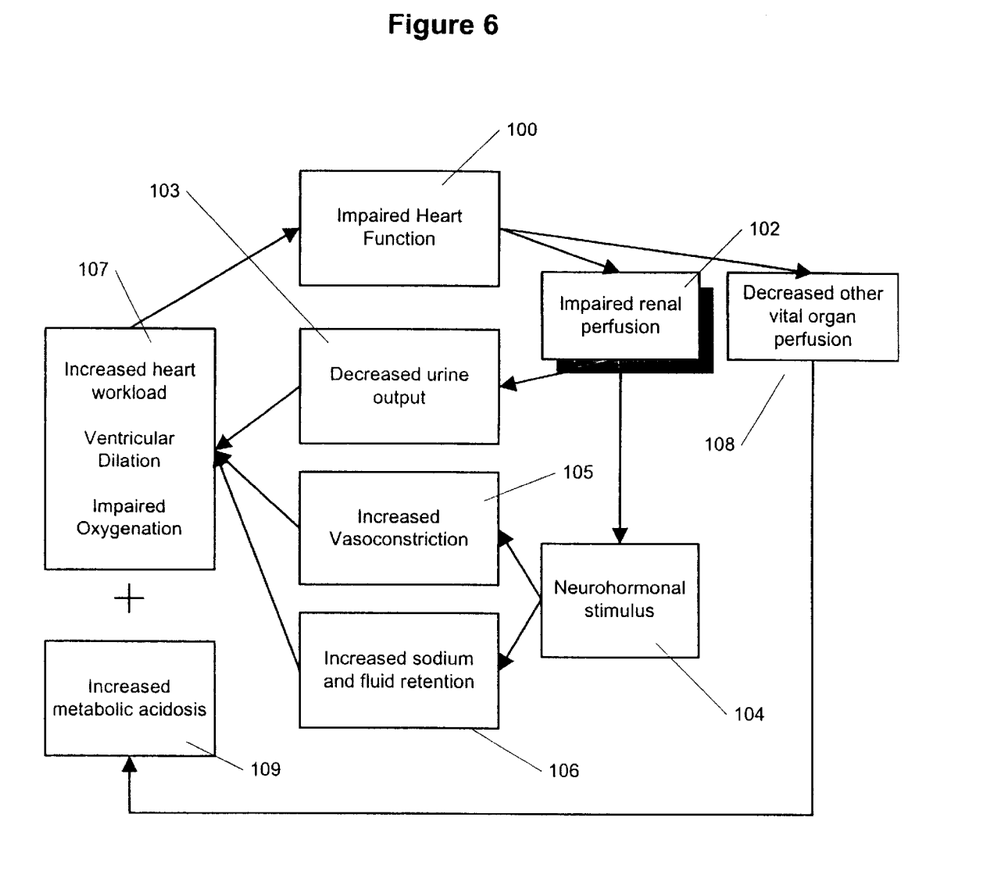
FIG. 6 is a flow diagram of the compensatory cycle of congestive heart failure.

FIG. 6 illustrates the hemodynamic impairment resulting from CHF. Impaired heart function 100 results in a decreased cardiac output, decreased peripheral blood pressure and diminished organ perfusion 102 and 108. The decrease in blood flow and consequent decrease in renal blood perfusion 102 activates several neurohomonal systems 104, such as the rennin-angiotensin and aldosterone system, sympatho-adrenal system and vasopressin release. As the kidneys suffer from increased renal vasoconstriction, the filtering rate (GFR) of the blood drops and the sodium load in the circulatory system increases 106. Simultaneously, more renin is liberated from the juxtaglomerular of the kidney 104. The combined effects of reduced kidney functioning include reduced glomerular sodium load, an aldosterone-mediated increase in tubular reabsorption of sodium, and retention in the body of sodium and water 106. These effects lead to several signs and symptoms of the CHF condition, including an enlarged heart (ventricular dilation), increased systolic wall stress and an increased myocardial oxygen demand 107, and the formation of edema on the basis of fluid and sodium retention in the kidney. Accordingly, sustained reduction in renal blood flow and vasoconstriction is directly responsible for causing the fluid retention associated with CHF.

FIG. 7 is a chart illustrating the remedial effects of direct renal infusion of a vasodilator. Increased fluid removal results from the restoration of renal blood flow 110 across the kidney by decreasing renal vascular resistance through renal vasodilation 110. Restoring renal perfusion 111, should result in increased urine output 112 and a decrease in the neurohormaonal stimulation 113 caused by kidneys in a failing condition. This decrease in stimulation by the kidneys is expected to decrease the vasoconstriction 114 in the patient's circulatory system, and decrease the amount of sodium and fluid retention 115 in the patient. In turn, increased urine output, reduced vasoconstriction, and decreased sodium level should restore normal fluid balances in the patient, improve oxygenation of the blood and decrease the heart workload 116. Heart function should improve 117 due to the reduction in its workload and the other beneficial effects due to renal perfusion. Moreover, a stronger heart and higher blood pressure will improve the perfusion of other organs 118 and thereby normalize the acid-base metabolism 119 to further improve the workload on the heart.

The level of effectiveness of this method is substantially above the levels achieved by systemic (IV or oral) drug therapy. A primary advantage of this method over other modalities is that the vasodilator compound is administered directly and locally to the kidney's arterial vasculature. This minimizes any untoward effects caused by systemic vasodilation and resultant increases in hypotension. In addition, a further advantage of this method is that the fluid overload in the patient is remediated by restoring the patient's own kidney function. This avoids relying on artificial kidney devices for hemofiltration or hemodialysis to remove excess body fluid and metabolic wastes.

The system for treating CHF disclosed here restores kidney functioning and thereby breaks the cycle between heart and kidney failure. This treatment may be used in connection with other CHF treatments that directly treat the heart, and may be used for both chronic and acute CHF.

The invention has been described in connection with what is presently considered to be the most practical and preferred embodiment. The invention is not limited to the disclosed embodiment. The invention covers various modifications and equivalent arrangements included within the spirit and scope of the appended claims.

What is claimed is:

1. A method for treatment of a patient suffering from reduced kidney function comprising the steps of:
   a. directly infusing at least one kidney of the patient with a fluid containing nitric oxide;
   b. by the application of the nitric oxide, increasing blood flow through the at least one kidney with resulting restoration of renal function of said kidney to a predetermined renal function level;
   c. after the nitric oxide passes through said at least one kidney, a vasodilator effect of said nitric oxide is reduced and does not cause increased blood flow through other body organs of the patient, and
   d. ceasing the infusion of nitric oxide after the predetermined renal functional level has been achieved.

2. A method of treatment of a patient having congestive heart failure comprising the steps of:
   a. directly infusing at least one kidney of the patient with a fluid containing nitric oxide;
   b. by the application of the nitric oxide, increasing blood flow through the at least one kidney with resulting restoration of renal function of said kidney to a predetermined renal function level;
   c. after the nitric oxide passes through said at least one kidney, a vasodilator effect of said nitric oxide becomes reduced and does not cause increased blood flow through other body organs of the patient, and
   d. ceasing the infusion of nitric oxide after the predetermined renal functional level has been achieved, wherein steps (a), (b) and (c) are repeated on a periodic basis to treat congestive heart failure.

3. A method as in claim 1 comprising the further step of perfusing the at least one kidney.

4. A method as in claim 1 wherein the fluid includes a carrier fluid.

5. A method as in claim 4 wherein the carrier fluid is selected from a group consisting of a saline solution, a krebs-ringer solution and a fluorocarbon emulsion.

6. A method of treatment of a patient having inadequate renal function comprising the steps of:
   a. preparing a vasodilator fluid by infusing a gas comprising nitric oxide into a carrier fluid externally of the patient;
   b. directly infusing at least one kidney of the patient with the vasodilator fluid;
   c. increasing blood flow through the kidney with resulting restoration of renal function of said kidney to a predetermined renal function level;
   d. ceasing the infusion of the vasodilator fluid after the predetermined renal functional level has been achieved.

7. A method of treatment of a patient suffering from inadequate renal function comprising the steps of:
   a. preparing an artificial vasodilator fluid by infusing a nitric oxide gas into a carrier fluid externally of the patient;
   b. directly infusing at least one kidney of the patient with the vasodilator fluid;
   c. increasing blood flow through the kidney with resulting restoration of renal function of said kidney to a predetermined renal function level;
   d. ceasing the infusion of the artificial vasodilation fluid after a predetermined renal functional level has been achieved.

8. A method as in claim 7 wherein the nitric oxide gas is infused through a membrane in contact with the carrier fluid at a rate dependent on a pressure of a nitric oxide gas source in fluid communication with the membrane.

9. A method to treat congestive heart failure in a patient comprising the steps of:
   a. directly infusing at least one kidney in the patient with a fluid containing a nitric oxide;
   b. increasing of blood flow through the kidney after step (a);
   c. ceasing step (a) after a predetermined renal functional level has been achieved, or a predetermined time of treatment has elapsed.

10. A method to treat congestive heart failure as in claim 9 wherein steps (a), (b), and (c) are repeated on a periodic basis to treat chronic congestive heart failure.

11. A method to treat congestive heart failure in a patient comprising the steps of:
    a. infusing at least one kidney in the patient with a fluid containing nitric oxide;
    b. ceasing the nitric oxide infusion step after a predetermined renal functional level has been achieved, or a predetermined time of treatment has elapsed.

12. A method to treat congestive heart failure as in claim 11 wherein steps (a) and (b) are repeated on a periodic basis to treat chronic congestive heart failure.

13. A method to treat a kidney in a patient having hypotension induced damage comprising the steps of:
    a. infusing the kidney with a fluid containing a vasodilator fluid comprising nitric oxide and a carrier fluid;
    b. increasing of blood flow through the kidney after step (a);
    c. after the nitric oxide passes through the kidney, a vasodilator effect of said nitric oxide becomes reduced and does not cause increased blood flow through other body organs of the patient, and
    d. ceasing step (a) after renal function has been restored.

14. A method as in claim 13 wherein step (a) is performed on said kidney and said patient has a second kidney that is not infused.

15. A method as in claim 13 wherein renal function restoration is determined by the patient achieving a predetermined renal functional level.

16. A method as in claim 13 wherein renal function restoration is determined by the patient achieving an increase in urine output.

17. A method as in claim 13 steps (a) and (b) are repeated on a periodic basis to treat recurring hypotension.

18. A method to treat chronic heart failure in a patient comprising the steps of:
    a. infusing a renal artery of the kidney with a fluid containing a nitric oxide, and
    b. increasing of blood flow through the kidney after step (a), wherein the nitric oxide becomes inactive in the patient promptly after flowing through the kidney.

19. A method as in claim 18 wherein the nitric oxide is scavenged by blood in the patient.

20. A method as in claim 18 wherein the nitric oxide becomes inactive before inducing systemic hypotension throughout the patient.

21. A method as in claim 4 wherein the carrier fluid is blood taken from the patient and further comprising the step of infusing nitric oxide gas into the blood externally of the patient.

22. A method as in claim 21 wherein the nitric oxide gas is mixed into the blood through a semi-permeable membrane externally of the patient.

23. A method as in claim 4 wherein the carrier fluid is plasma taken from the patient and further comprising the step of infusing the nitric oxide into the plasma externally of the patient.

24. A method as in claim 1 wherein the nitric oxide is substantially eliminated from blood with 10 seconds after infusion into the kidney.

25. A method of treatment of a patient having reduced renal function comprising the steps of:
    a. preparing a vasodilator solution comprising nitric oxide and carrier fluid;
    b. infusing the vasodilator solution into at least one kidney of the patient;
    c. the infusion of the vasodilator solution increases blood flow through the at least one kidney with resulting restoration of renal function of said kidney;
    d. ceasing the artificial vasodilatation step after a predetermined renal functional level has been achieved.

26. A method of treatment of a patient suffering from reduced kidney function comprising the steps of:
    a. infusing at least one kidney of the patient with a vasodilator solution comprising nitric oxide that releases all nitric oxide upon contact with blood in the kidney, and
    b. ceasing releasing nitric oxide after the blood treated with the infusion of said vasodilator solution passes through the infused kidney.

* * * * *